(12) United States Patent
Myogadani

(10) Patent No.: US 6,562,232 B2
(45) Date of Patent: May 13, 2003

(54) FRACTIONATING APPARATUS

(75) Inventor: Toru Myogadani, Yokohama (JP)

(73) Assignee: Moritex Corporation, Tokyo (JP)

( * ) Notice: Subject to any disclaimer, the term of this patent is extended or adjusted under 35 U.S.C. 154(b) by 16 days.

(21) Appl. No.: 09/922,795

(22) Filed: Aug. 7, 2001

(65) Prior Publication Data

US 2002/0043489 A1 Apr. 18, 2002

(30) Foreign Application Priority Data

Aug. 8, 2000 (JP) ........................................ 2000-239999

(51) Int. Cl.[7] .............................................. B01D 17/12
(52) U.S. Cl. ...................... 210/94; 210/198.2; 422/63; 422/69; 422/70; 422/82.05; 422/100; 422/101; 422/103
(58) Field of Search ............................ 210/87, 94, 96.1, 210/97, 104, 198.2, 656–659, 745; 436/161, 164, 174, 178, 180; 422/62, 63, 69, 70, 82.05, 101, 100, 103

(56) References Cited

U.S. PATENT DOCUMENTS

| | | | | |
|---|---|---|---|---|
| 6,080,318 A | * | 6/2000 | Gumm et al. | 210/656 |
| 6,197,198 B1 | * | 3/2001 | Messinger et al. | 210/656 |
| 6,210,571 B1 | * | 4/2001 | Zambias et al. | 210/656 |
| 6,355,164 B1 | * | 3/2002 | Wendell et al. | 210/656 |
| 6,461,515 B1 | * | 10/2002 | Safir et al. | 210/656 |

* cited by examiner

Primary Examiner—Joseph Drodge
(74) Attorney, Agent, or Firm—Greenblum & Bernstein, P.L.C.

(57) ABSTRACT

Fractionating apparatus having a plurality of sample elution system ($S_1$–$S_8$) in which a nozzle (N) movable in the direction of the row of fractionation vessels (4, 4, ---) arranged in a matrix is disposes to each of the sample elution system ($S_1$–$S_8$) and kept standing-by just above an empty fractionation vessel (4), a valve (30) is operated when elution of sample ingredients is detected by photosensor ($PD_1$–$PD_8$) to drop the sample ingredients to the fractionation vessel (4, 4, ---) and the nozzle is moved after dropping the sample ingredient by a required amount, and in which the nozzle (N) and the valve (30) can be operated individually on every sample elution systems at different timings respectively such that the eluate can be dropped at different timing on every sample elution systems.

6 Claims, 5 Drawing Sheets

FRACTIONATING APPARATUS

BACKGROUND OF THE INVENTION

1. Field of the Invention

The present invention concerns a fractionating apparatus for eluting samples from a plurality of columns simultaneously and dropping ingredients thereof successively each by a required amount to fractionation vessels in each of rows arranged in a matrix.

2. Statement of the Related Art

When a novel compound is prepared by combining several substances, a combinatorial chemistry has been adopted recently. In this method, several kinds of materials provided previously are mixed at different mixing ratios on every vial tubes to cause chemical reactions and synthesized a number of synthesized samples simultaneously.

A fractionating apparatus is used for purifying the thus synthesized samples and analyzing ingredients contained therein and fractionating only the optional effective ingredients.

The fractionating apparatus is adapted to fractionate the ingredients of a sample by injecting a sample to a column filled with an adsorbent such as silica, supplying a solvent from one end of the column and eluting the ingredients of the sample from the other end, depending on the difference in the elution time between each of the ingredients.

However, since several tens kinds of samples are synthesized simultaneously in the combinatorial chemistry, if fractionation is conducted on every samples, it takes as much as 6 to 7 hours for only fractionating samples even of ten kinds of them if column exchange time or the like is taken into consideration.

In view of the above, it has recently been proposed a fractionating apparatus comprising a plurality of sample elution systems in which a plurality of columns (10 to 16) are set simultaneously, a solvent is supplied at the same time to each of the columns and sample ingredients are eluted simultaneously.

According to this apparatus, since sample ingredients from the respective columns can be fractionated simultaneously by successively dropping samples eluted from each of sample elution systems in a time sequential manner into fractionation vessels in each of the rows arranged in a matrix, fractionation time can be shortened and column exchanging labor and time can also be saved.

However, since elution time is different due to the difference of the ingredients contained in each of the samples, it may sometimes occur that while sample ingredients are eluted from one column, sample ingredients are not yet eluted from other columns.

Further, the number of sample ingredients to be fractionated is different between a sample containing a large number of ingredients and a sample at a relatively high impurity with less number of ingredients.

That is, when a large number of ingredients are contained, it is necessary to reliably fractionate each of the ingredients by decreasing the amount of a solvent to be dropped to one fractionation vessel. An extremely large number of ingredients can not sometimes be coped with fractionation vessels only for one row but increase of the number of fractionation vessels in each row makes the size of the fractionating apparatus larger.

On the other hand, for a compound at a relatively high purity, it may suffice to fractionate only the portion at a high concentration of the ingredient when it is eluted, and it is not necessary to fractionate other portion at an extremely low concentration in which the aimed ingredient is not eluted.

As described above, when plurality of sample elution systems are merely provided irrespective of the difference for the timing of dropping ingredients or the amount of dropping to individual fractionation vessels in accordance with samples, eluates are dropped evenly from all of the sample elution systems into fractionation vessels, to result in a problem that the substances can not be fractionated in accordance with the ingredients contained in each of the samples.

In view of the above, it is a technical subject of this invention to enable each of the ingredients to be dropped at an optional timing on each of the sample elution systems to the fractionation vessels in each of rows in a case of providing a plurality of sample elution systems. It is a second subject of this invention to enable reliable fractionation to the last without enlarging the size of the fractionating apparatus in a case where the number of ingredients is large and can not be coped with the fractionation vessels only for one row.

SUMMARY OF THE INVENTION

For overcoming the subjects described above, this invention provides a fractionating apparatus having a required number of sample elution systems adapted to elute samples adsorbed on columns and successively drop the sample ingredients contained therein into fractionation vessels arranged in a matrix, in which each of the sample elution systems comprises a nozzle for dropping eluted sample ingredients into fractionation vessels, a drain for discharging unnecessary solvent, a valve for switching the nozzle and the drain and a driving mechanism for reciprocating each of the nozzles independently of each other along the direction of the row of the fractionation vessels, and a photosensor is disposed to the upstream of the valve for detecting the presence or absence of the sample ingredients contained in the solvent flowing in the sample elution systems and a control device is disposed for successively stopping each of the nozzles at a location just above the fractionation vessel by each of the driving mechanisms and opening the valves while a sample ingredient to be fractionated is being eluted, on the basis of the detection signal from the photosensor and the flow rate of the solvent.

According to this invention, since each of the nozzles is moved along fractionation vessels in each row by each of the driving mechanism, stopped just above an empty vessel and kept standing-by until elution of the sample ingredient is detected by the photosensor disposed to each of the sample elution systems, during which the solvent discharged from the columns is discarded to the drain.

When the elution of the sample ingredient is detected, the valve corresponding to the sample elution system is operated and the ingredient is dropped by the dropping nozzle from the fractionation vessel and the ingredient is fractionated.

Then, when the eluate is eluted by a required amount, the nozzle is moved to the next fractionation vessel and drops other sample ingredient again.

As described above, the nozzle is moved successively when the detection signal is outputted from the photosensor and the ingredient is dropped each by required amount and the ingredients are dropped successively to the fractionation vessels arranged in the direction of the row. Thus, a larger number of fractionation vessels are used when the number of ingredients is large since the output frequency for the detection signals is high, whereas a less number of fractionation vessels are used when the number of ingredients is small. Since the nozzle and the valve are operated individually on every sample elution systems, ingredients can be dropped at different timings respectively.

Since the valve is operated based on the detection signals of each of the photosensors in each of the sample elution systems, when only the solvent is discharged with no elution of the ingredients, it is discharged into a drain as it is and only when the ingredient is eluted, the ingredient can be dropped into the fractionation vessel, so that wasteful collection only for the solvent to the fractionation vessel can be avoided.

In a preferred embodiment, according to this invention, nozzles which are opened or made conductive selectively by the valve are disposed each by two on each of the sample elution systems and each of the nozzles is reciprocated together over the adjacent rows of the fractionation vessels arranged in a matrix and in the direction of the row by the driving mechanisms.

According to this preferred embodiment, when sample ingredients are fractionated, they are successively dropped from the nozzle on one side into the fractionation vessels in one row during forwarding stroke while they are dropped successively from the nozzle on the other side to the fractionation vessels in the other row during backwarding stroke, by which ingredients are fractionated divisionally into fractionation vessels in two rows, and this can cope with a case requiring a large number of fractionation vessels.

In this case, it is not necessary to move the nozzles in the lateral direction but they only have to be moved reciprocally, the structure of the nozzle driving mechanism can be made simple to reduce the worry of failure.

Further, while the number of the fractionation vessels increases in the lateral direction, since the nozzles are made reciprocatable individually in the direction of the row, the width of the driving mechanism is about twice the diameter of the fractionation vessels, so that the lateral size changes scarcely even when the number of fractionation vessels is increased by one row between the rows.

DESCRIPTION OF THE ACCOMPANYING DRAWINGS

Figure 4:
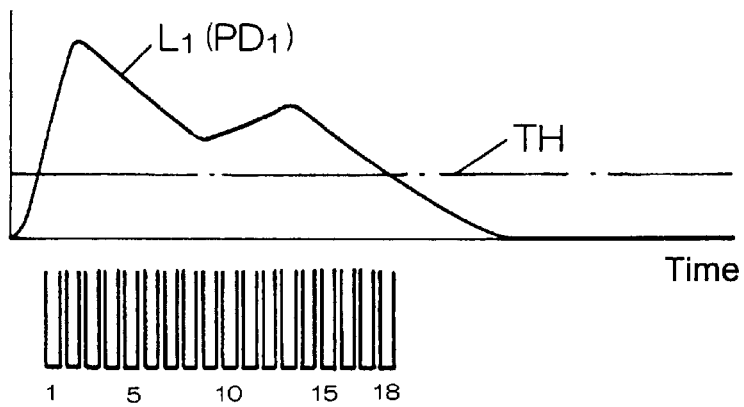
Figure 4:
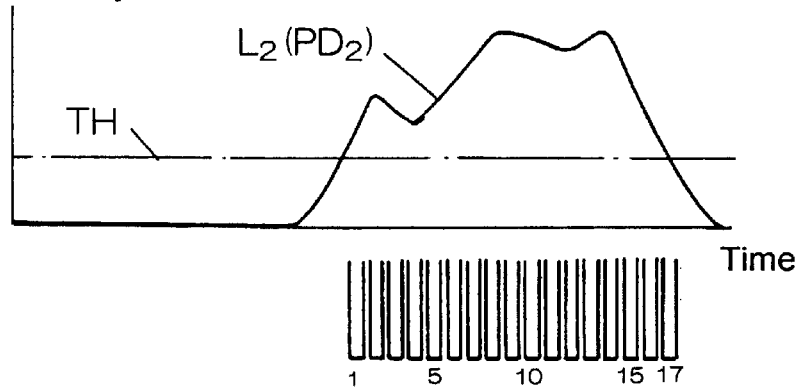
Figure 4:
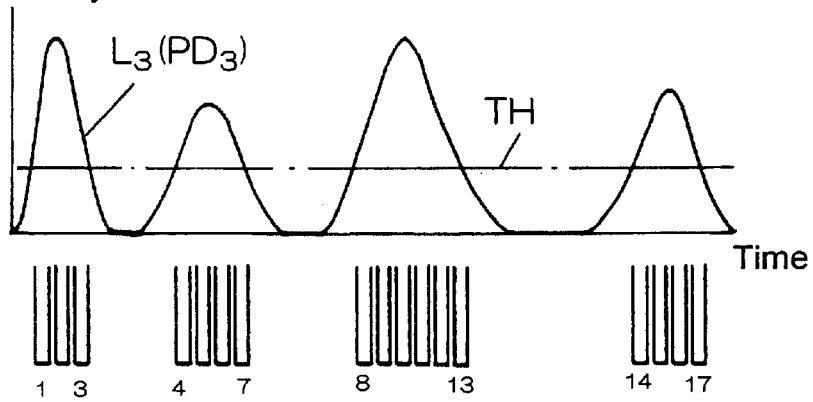
Figure 5:
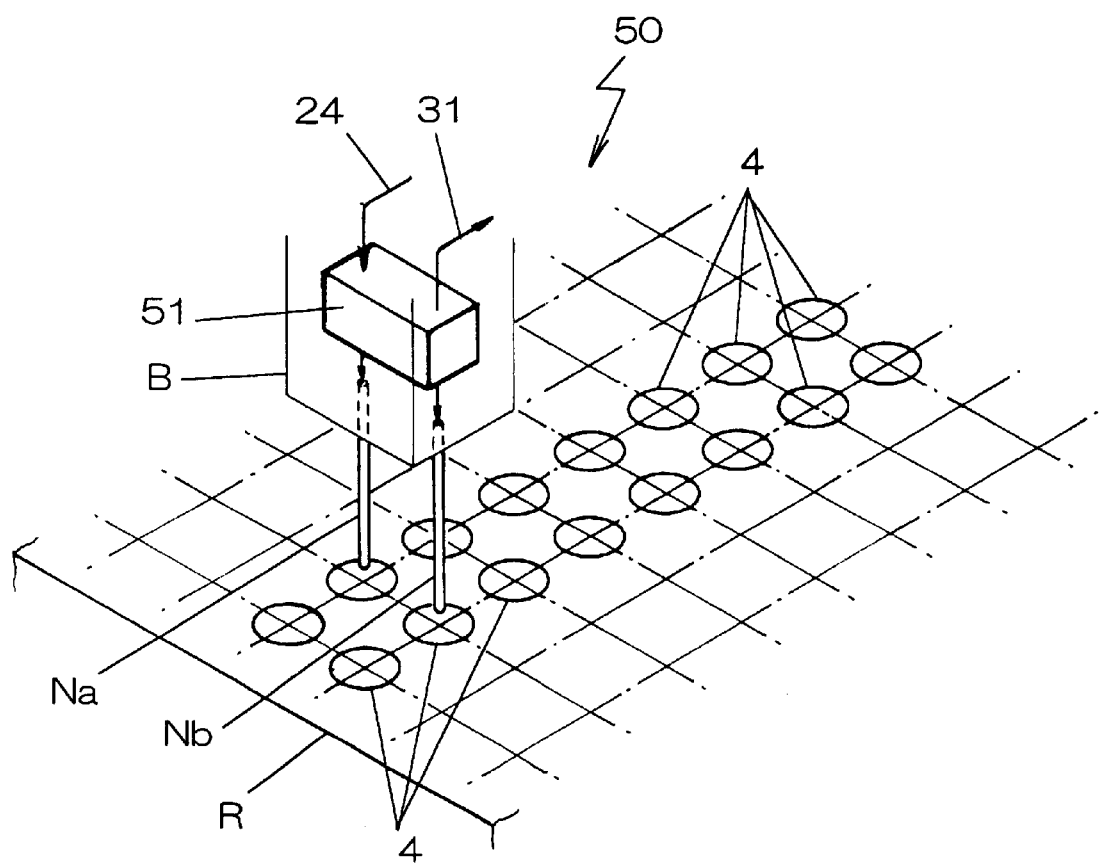

FIGS. 4(a)–4(c) are graphs illustrating examples of elution timing of sample ingredients; and FIG. 5 is a schematic explanatory view illustrating a main portion of an other embodiment.

DESCRIPTION OF PREFERRED EMBODIMENT

This invention will be explained by way of preferred embodiments with reference to the drawings.

Figure 1:
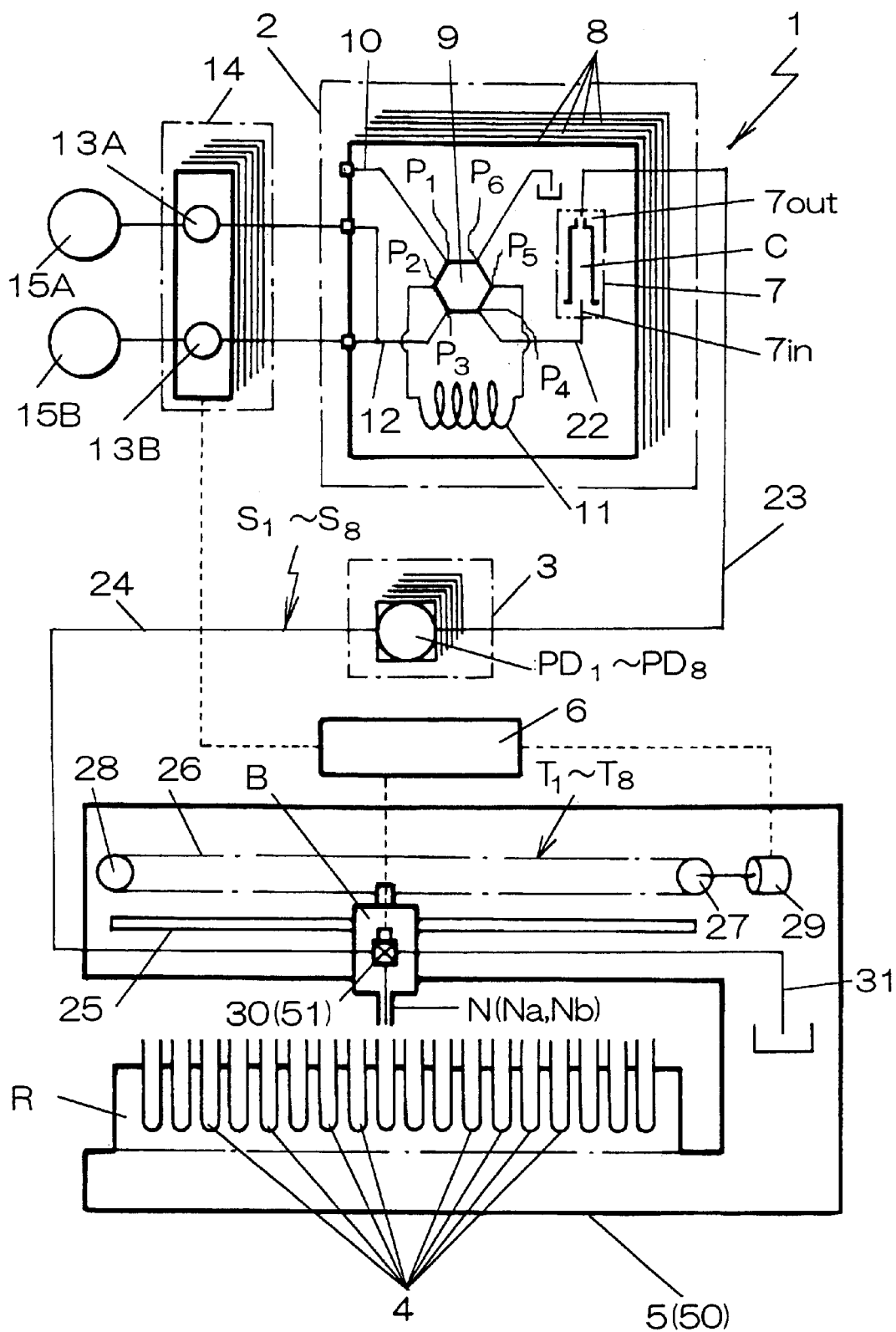
FIG. 1 is a schematic view illustrating a fractionating apparatus according to the present invention.
Figure 2:
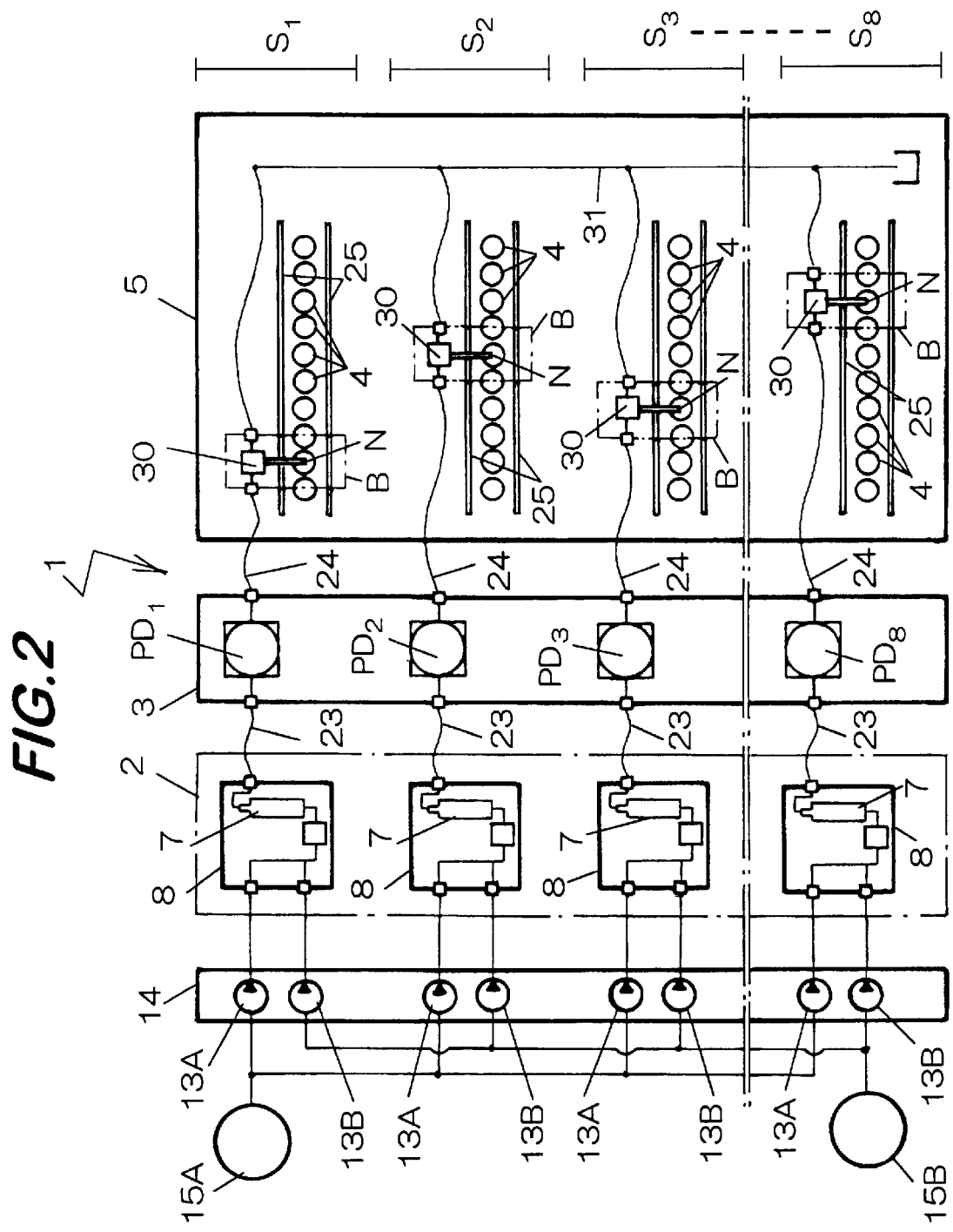
FIG. 2 is an explanatory view illustrating a flowing route in an entire apparatus.
Figure 3:
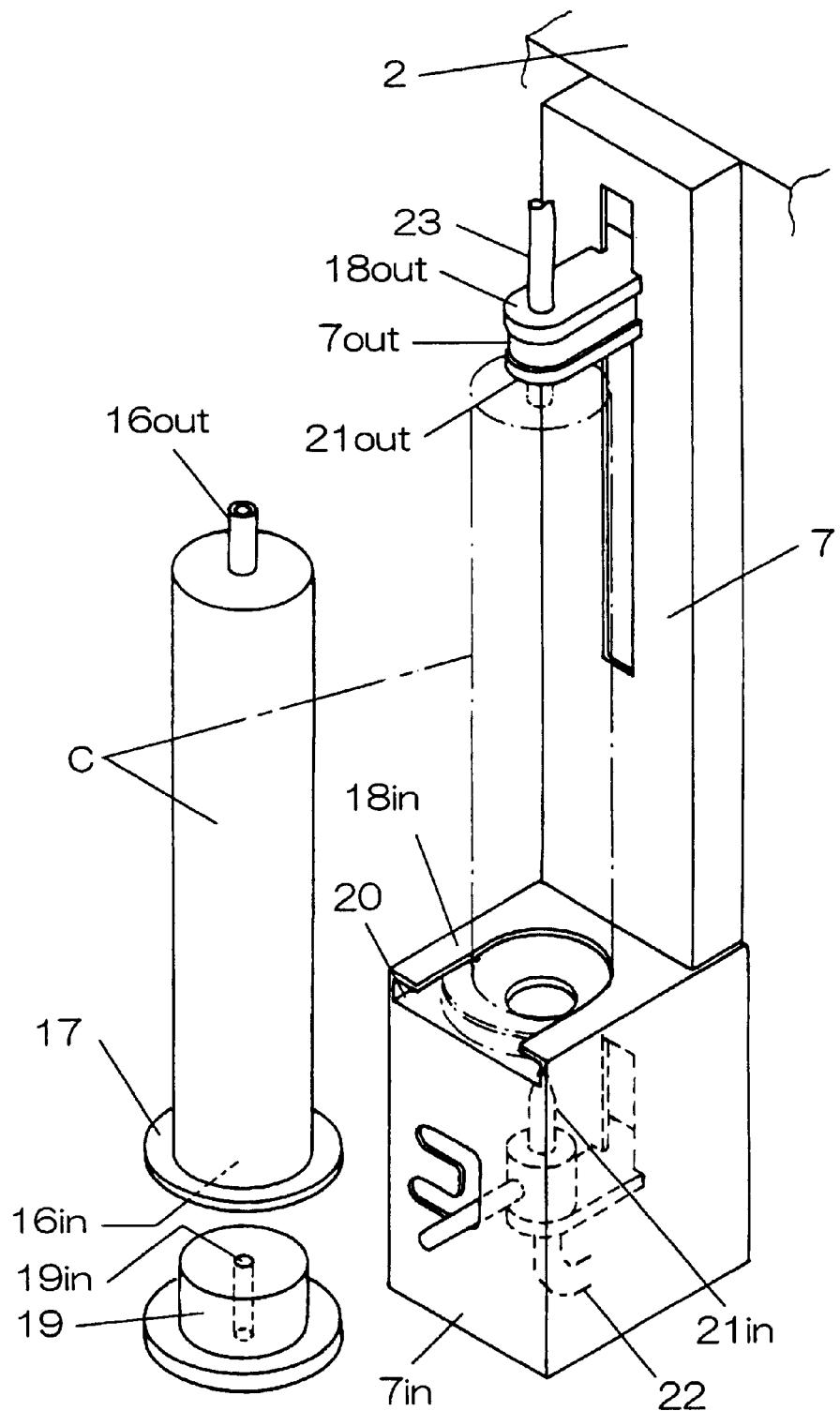
FIG. 3 is an explanatory view illustrating a column stand.

A fractionating apparatus shown in FIG. 1 comprises a column stand 2 for supplying a solvent to columns C, C, in which samples are adsorbed to elute sample ingredients, a detection device 3 for detecting whether the sample ingredient is contained or not in the solvent discharged from each of the columns C, C, --- by UV-ray sensors $PD_1$ to $PD_8$, a fraction collector 5 for successively dropping the sample ingredients to test tubes (fractionation vessels) 4, 4, --- in each of rows arranged in a 20×8 matrix and a control device 6 for controlling the fraction collector 5 based on the direction signals from the detection device 3.

Then, eight sample elution systems $S_1$–$S_8$ are formed to the fractionating apparatus 1 for successively dropping sample ingredients passed from each of the columns C, C, --- through each of the detection devices 3 and then eluted into test tubes (fractionation vessels) 4, 4, --- in each row arranged in the fraction collector 5.

The column stand 2 comprises column holders 7, 7, for holding each of the columns C, C, filled with an adsorbent such as silica, and each of the fluid circuits 8, 8 --- for supplying samples to each of the columns C, C, --- held in the holders 7, 7, --- to adsorb them and supplying the solvent to elute the sample ingredients.

A six-way valve 9 is interposed in the fluid circuit 8 for switching the flow channel, in which the port $P_1$ is connected with a sample supply flow channel 10, ports $P_2$ and $P_5$ are connected with a sample loop 11 for storing a predetermined amount of sample in the flow channel, a port $P_3$ is connected with a solvent supply flow channel 12, port $P_4$ is connected with an entrance 7 in of the column holder 7 and a port $P_6$ is connected with a drain 8d, respectively.

The six-way valve 9 is adapted to communicate the ports $P_1$ and $P_2$, and the ports $P_5$ and $P_6$ to inject the sample by way of the sample supply channel 10 to store the sample in the sample loop 11 and then switch the flow channel to communicate the ports $P_3$ and $P_2$ and the ports $P_5$ and $P_4$ to extrude the sample by the solvent supplied from the solvent supply flow channel 12 to each of the columns C, C, --- and adsorb the sample in the columns.

Further, upon elution, the solvent is supplied further while maintaining the flow channel as it is, whereby each of the ingredients of the sample adsorbed to each of the columns C, C, --- is sent from the exit $7_{in}$ of the column holder 7 to the detection device 3.

The solvent supply flow channel 12 is connected on each of elution systems $S_1$ to $S_8$ by way of a pump unit 14 having a pair of pumps 13A and 13B to two solvent reservoirs 15a and 15b storing different solvents so as to supply the solvents at a predetermined mixing ratio from the reservoirs 15A and 15B.

Further, each of the columns C is provided with a flange 17 at an entrance $16_{in}$ and with an exit $16_{out}$ of a fine diameter like that an injection syringe. Each of the column holders 7, 7, --- is provided with a chuck $18_{in}$ and $18_{out}$ at the entrance $7_{in}$ and the exit $7_{out}$ for fixing the entrance $16_{in}$ and the exit $16_{out}$ of each of the columns C.

The chuck $18_{in}$ at the entrance $7_{in}$ is formed with a groove 20 which receives the flange 17 and an adapter 19 for the adjustment of the diameter, with the adapter 19 being fitted to the inlet $16_{in}$ of the column C. An injection nozzle $21_{in}$ is mounted to the column C vertically movably into and out of the entrance hole $19_{in}$ perforated in the adapter fixed to the groove 20.

Further, the chuck $18_{out}$ at the exit $7_{out}$ is positioned adjustably along the longitudinal direction of the column C, and has a port $21_{out}$ fitted externally to the exit $16_{out}$. Flexible pipes 22 and 23 are connected with the entrance $7_{in}$ and the exit $7_{in}$. The column holder 7 can be set optionally with the entrance $7_{in}$ and the exit $7_{out}$ turned upside down.

The column stand 2 is connected by way of the flexible pipe 23 to the detection device 3 and further connected by way of the flexible pipe 24 to the fraction collector 5.

The fraction collector 5 comprises test tubes 4, 4, --- arranged in a matrix on a rack R, and needle nozzles N, N --- for successively dropping sample ingredients from above the rack into each of the test tubes 4. The nozzles N, N, --- are attached to bases B moving along tracks (driving mechanism) $T_1$–$T_8$ formed in the direction of the rows of the test tubes 4, 4, ---.

Each of the tracks $T_1$–$T_8$ has a guide rail 25 for guiding the base B, an endless belt 26 for moving the base along the guide rail 25, pulleys 27 and 28 around which the belts are laid and a motor 29 for rotating the pulley 27 forwardly and backwardly.

Further, a three-way valve 30 is mounted on each of the bases B, in which the flexible pipe 24 is connected to the entrance and the needle nozzle N and a drain 31 are connected to the exit such that they are selectively in communication.

The control device 6 collectively controls the fractionating apparatus 1. That is, the device 6 is adapted to control each of the pumps 13A and 13B of the pump unit individually to control the rate of change of the flow rate and the mixing ratio of respective solvents to be supplied from the solvent reservoirs 15A and 15B to each of the every sample elution systems $S_1$–$S_8$, and rotate each of the motors 29 in each of tracks $T_1$–$T_8$ individually based on detection signals from the UV-ray photosensors $PD_1$–$PD_8$ of the detection device 3, to open/close each of the three-way valves 30 individually.

Then, when the elution of the sample ingredient is detected by each of the UV-ray photosensors $PD_1$–$PD_8$, the device opens the three-way valve 30 and drops the sample ingredient into the test tube 4 through the needle nozzle N after the lapse of a predetermined time calculated based on the volume of the flexible pipe 24 and the total flow rate of the solvents supplied to each of the sample elution systems $S_1$–$S_8$.

Then, after the lapse of a time required for dropping a predetermined amount of the ingredient, the three-way valve 30 is closed momentarily to shut the needle nozzle and, at the same time, the needle nozzle N is moved just above the next test tube 4 and the three-way valve 30 is opened. The sample ingredients can be dropped successively by repeating this procedure. When the sample ingredient is no longer detected by the UV-ray photosensors $PD_1$–$PD_8$, the three way valve 30 is switched to the drain 31 after the lapse of a predetermined time to shut the needle nozzle N.

Thus, since only the solvent containing the sample ingredients is fractionated in the test tubes 4 and the solvent not containing the sample ingredients is discarded, the test tube 4 is no more used unnecessarily.

An example for the constitution of the present invention is as has been described, above and the function thereof is to be explained.

At first, empty columns C, C, --- are attached to the column holders 7, 7, ---, the six-way valves 9 of the column stand 2 are operated to open the flow channel from the sample supply flow channels 10 to the sample loops 11. When a previously synthesized sample is injected by a required amount from the sample supply flow channel, the sample is stored in the sample loop 11.

Then, when the six-way valve 9 is switched to open the flow channel from the solvent supply flow channel 12 through the sample loop 11 to the entrance 7$_{in}$ of the column holder 7 and each of the pumps 13A and 13B of the pump unit 14 is actuated to supply the solvents from the solvent bottles 15A and 16A respectively, the sample in the sample loop 11 is extruded by the solvent and sent to the column C and adsorbed to the adsorbent such as silica filled in the column C.

Then, when the solvent is supplied further, the ingredients contained in the sample adsorbed to the column C are successively eluted time sequentially from those of less adsorption on every sample elution systems $S_1$–$S_8$.

In this case, it is customary to store a solvent of a relatively low eluting effect and a solvent of a relatively high eluting effect in each of the solvent reservoirs 15A and 15B and the mixing ratio is provided with a gradient such that the concentration of the solvent of higher eluting effect is gradually increased continuously. The solvent may also be discharged always at a predetermined concentration. The mixing ratio control is conducted by the flow rate control of the control device 6 that variably controls the number of rotation of each of the pumps 13A and 14A of the pump unit 14.

FIGS. 4(*a*)–(*c*) are graphs showing the result of detection by the photosensors. Illustrated graphs show the result by the photosensors $PD_1$–$PD_3$ among the photosensors $PD_1$–$PD_8$ of the detection device 3, in which curves $L_1$–$L_3$ show absence or presence of the eluted sample ingredients and the light intensity increases as the sample ingredient is eluted.

According to this example, the ingredients contained are different depending on the samples and it can be seen that each of the ingredients is eluted at different timing also in view of the result of the detection by each of the photosensitive $PD_1$–$PD_3$.

For example, in a case of the sample elution system $S_1$ (FIG. 4(*a*)), since it contains a greater amount of ingredients that are eluted relatively easily, the ingredients contained in the sample start elution as soon as the solvent is supplied.

Further, in a case of the sample solution system $S_2$, as shown in FIG. 4(*b*), since it contains a greater amount of less eluting ingredients, ingredients contained in the sample are not dissolved instantly upon supply of the solvent but elution is started somewhat later.

Further, in a case of the sample solution system $S_3$, as shown in FIG. 4(*c*), easily eluting ingredients and less eluting ingredients are present mixed together and elution of the ingredients occurs intermittently.

A horizontal line $T_1$ indicates a threshold level as a reference value for judging absence or presence of elution of sample ingredients worth while to be collected and a sample ingredient is fractionated when the optical intensity distribution is higher than the threshold value.

Then, in the fraction collector 5, the control device 6 controls the motor 20 for driving the base B in each of the tracks $T_1$–$T_8$ and the three-way valve 30 for opening or shutting each of the needle nozzles N individually at optional timing based on the result of the detection by each of the photosensors $PD_1$–$PD_8$. In each of the sample elution systems $S_1$ to $S_8$, the needle nozzle N is positioned to the test tube 4 at the top of each row.

Then, in the sample elution system $S_1$, ingredients contained in the sample start elution as soon as the solvent is supplied. When the elution is detected by the UV-ray photosensor $PD_1$, the three-way valve 30 is opened after the lapse of a predetermined time at which the ingredient reaches the three-way valve 30 attached to the base B of the track $T_1$, and the sample ingredients are dropped from the needle nozzle 4 into the test tube 4 at the top of first row.

Then, when opening/closure of the three-way valve 30 are repeated on every dropping of the ingredient by a required amount and the needle nozzle N is moved to a location just above the adjacent test tube 4 while the shutting of the needle nozzle N is being shut. By repeating the procedures, the sample ingredients can be dropped successively to the test tubes till the ingredients are eluted no more.

On the other hand, in the sample elution system $S_2$, since the ingredients contained in the sample are not eluted for a while even after the supply of the solvent, the system is kept standing-by till the sample ingredients are detected by the UV-ray photosensor $PD_2$. When there are detected, sample ingredients are successively dropped to the test tubes 4 in the second row while opening/closing the threeway valve 30 attached to the base B of the track $T_2$ in the same manner as that in the sample elution system $S_1$.

Further, in the sample elution system $S_3$, when the sample ingredients are detected by the UV-ray photosensor $PD_3$, the control device opens the three-way valve 30 mounted on the base B of the track $T_3$ after the lapse of a predetermined time, closes the three-way valve 30 when the sample ingredients are no more detected, moves the needle nozzle N to a location just above the adjacent test tube 4 and, when the sample ingredients are detected, opens the three-way valve again. By repeating the procedures, the sample ingredients are successively dropped into the tubes 4 in the third row.

As described above, even when the sample ingredients are eluted at different timings on every sample elution systems $S_1$–$S_3$, the control device 6 controls the motor 29 for driving the base B of each of the tracks $T_1$–$T_8$ and the threeway valve 30 for opening or shutting each of the needle nozzles N individually.

Accordingly, irrespective of the timings at which the sample ingredients are eluted, it is possible to discard the solvent not containing the sample ingredients individually into the drain 31 and successively drop only the solvent containing the sample ingredients to the test tube 4, 4 --- in each of the rows in any of the sample elution systems $S_1$–$S_8$.

FIG. 5 shows an another preferred embodiment according to this invention. Portions or sections identical with those in FIG. 1 carry the same reference numerals for which duplicate explanations will be omitted.

In this preferred embodiment, a fraction collector to shown in FIG. 5 is used instead of the friction collector 5 of the fractionating apparatus 1.

In the rack R of the fraction collector 50, test tubes 4, 4, --- are arranged by 16 rows, which are twice of 8 rows in the sample elution systems $S_1$–$S_8$, that is, in 20×16 matrix.

Even when the number of the test tubes 4, 4, --- is doubled, since each of the tracks $T_1$–$T_8$ for reciprocating the base B has a lateral width about twice the diameter of the test tube 4 (e.g., 1 cm), the lateral width of the rack R is not enlarged by so much even when the test tubes 4, 4 --- are arranged by two rows just below each of the tracks $T_1$–$T_8$.

Then, two nozzles Na and Nb that are opened selectively by a valve 51 are situated at the location above adjacent rows of the test tubes 4, 4, --- arranged in a matrix and reciprocated together along the direction of the row. As the valve 51, a 1-input/3-output direction control valve or three-way valves in a dual arrangement may be used.

Then, when the sample ingredients are fractionated by reciprocating the base B for each of the tracks $T_1$–$T_8$, the sample ingredients are dropped successively from the needle nozzle Na on one row of the test tubes 4, 4, --- during forwarding stroke, while the sample ingredients are dropped successively from the needle nozzle Nb on the other adjacent row of the test tubes 4, 4, --- during backwarding stroke.

Accordingly, the sample ingredients can be fractionated into 40 test tubes 4, 4 --- in two-rows by the number 40, and there is no requirement for using a large scaled fractionating apparatus even if the sample contain a large number of ingredients, and a small size of refining separation may be used.

This embodiment is identical with the fractionating apparatus 1 shown in FIG. 1 in that the control device 6 controls the motor 29 for reciprocating the base B of each of the tracks $T_1$–$T_8$, a valve 51 for selectively opening the needle nozzles Na and Nb based on the detection signals from the detection device 3.

As has been described above according to the present invention, since sample ingredients can be dropped successively each at an optional timing to each of the fractionating vessels arranged in a matrix even in a case where the elution timing for the sample ingredients is different on every sample elution systems, it is possible to fractionate only the solvent containing the sample ingredients while discarding the solvent not containing the sample ingredients on every sample elution systems, and it can provide an excellent effect capable of using fractionation vessel effectively with no less.

Further, when nozzles opened selectively are formed each by two in each of the sample elution systems and each of the nozzles is reciprocated together along the direction of the adjacent rows of the fractionating vessels arranged in a matrix, since the sample ingredients can be dropped from the nozzles on one side to the fractionation vessels in one row during movement in the forward channel while the ingredients can be dropped successively from the nozzle on the other side to the fractionating vessels in the other row during movement in the backward channel, it can provide an excellent effect capable of reliably fractionating the ingredients to the last when the number of ingredients is large and can not be coped with fractionating vessels in one row, without enlarging the size of the repetitive device.

The present disclosure relates to subject matter contained in priority Japanese Patent Application No. 2000-239999, filed on Aug. 8, 2000, the contents of which is herein expressly incorporated by reference in its entirety.

What is claimed is:

1. A fractionating apparatus having a plurality of sampling elution systems adapted to elute samples adsorbed on columns and successively drop the sample ingredients contained therein into fractionation vessels, having a diameter, arranged in a matrix, in which each of the sample elution systems comprises a nozzle for dropping eluted sample ingredients into fractionation vessels, a drain for discharging unnecessary solvent, a valve for switching between the nozzle and the drain and a driving mechanism for reciprocating each of the nozzles independently of each other along the direction of a row of the fractionation vessels, and a photosensor is disposed upstream of the valve for detecting the presence or absence of the sample ingredients contained in the solvent flowing in the sample elution systems; and a control device is disposed for successively stopping each of the nozzles at a location just above the fractionation vessels by each of the driving mechanisms and opening the valve while a sample ingredient to be fractionated is being eluted, on the basis of at least the detection signal from the photosensor.

2. A fractionating apparatus as defined in claim 1, wherein nozzles which are opened selectively by the valve are disposed each by two on each of the sample elution systems and each of the nozzles is reciprocated together over the adjacent rows of the fractionation vessels arranged in a matrix and in the direction of the row by the driving mechanisms.

3. The fractionating apparatus as defined in claim 1, wherein the driving mechanism has a width, and said width of the driving mechanism is about twice the diameter of the fractionation vessels.

4. The fractionating apparatus as defined in claim 1 comprising two rows of fractionation vessels.

5. The fractionating apparatus as defined in claim 1, wherein the photosensor comprises UV-ray photosensor.

6. The fractionating apparatus as defined in claim 1, comprising a six-way valve.

* * * * *